United States Patent [19]

Ito et al.

[11] Patent Number: 4,988,704
[45] Date of Patent: Jan. 29, 1991

[54] PYRIMIDINE DERIVATIVE, PROCESS FOR PREPARING SAME AND ARGICULTURAL OR HORTICULTURAL FUNGICIDAL COMPOSITION CONTAINING SAME

[75] Inventors: Shigekazu Ito; Katsumi Masuda; Shoji Kusano; Toshihiro Nagata; Yoshiyuki Kojima; Nobumitsu Sawai; Shin-ichiro Maeno, all of Shizuoka, Japan

[73] Assignees: Kumiai Chemical Industry Co., Ltd.; Ihara Chemical Industry Co., Ltd., both of Japan

[21] Appl. No.: 325,808

[22] Filed: Mar. 20, 1989

Related U.S. Application Data

[63] Continuation of Ser. No. 924,384, Oct. 29, 1986, Pat. No. 4,814,338.

[30] Foreign Application Priority Data

Oct. 30, 1985 [JP] Japan ................... 60-243476
Jul. 29, 1986 [JP] Japan ................... 61-178354

[51] Int. Cl.$^5$ ................... A01N 43/54; C07D 239/34
[52] U.S. Cl. ................... 514/275; 544/322; 544/326; 544/330
[58] Field of Search ................... 514/256, 275; 544/330, 544/322, 326

[56] References Cited

U.S. PATENT DOCUMENTS

| 3,499,898 | 3/1970 | von Bebenburg et al. | 544/322 |
| 4,427,437 | 1/1984 | Serban et al. | 544/311 |
| 4,659,363 | 4/1987 | Hubele et al. | 71/92 |

FOREIGN PATENT DOCUMENTS 1245085  9/1971  United Kingdom ................... 544/322

OTHER PUBLICATIONS

Chemical Abstracts, vol. 96, No. 19, Abstract 157,395n, pp. 273–274, May 10, 1982, (Franke et al.).

European Search Report EP 86 30 8422 dated December 12, 1987.

Primary Examiner—Mary C. Lee
Assistant Examiner—Zinna Northington-Davis
Attorney, Agent, or Firm—Sughrue, Mion, Zinn, Macpeak & Seas

[57] ABSTRACT

Disclosed are pyrimidine derivatives represented by general formula

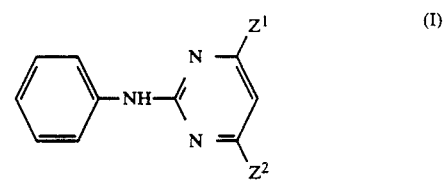

wherein $Z^1$ represents an alkynyl group, an alkenyl group, an alkoxy group, an alkenyloxy group, or an alkynyloxy group which may be substituted with a halogen atom, and $Z^2$ represents a hydrogen atom, a halogen atom, an alkyl group, an alkoxy group, or a group of the formula

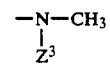

where $Z^3$ represents a hydrogen atom or a methyl group; or its salt, and processes for preparing same. Also, agricultural or horticultural compositions containing the pyrimidine derivatives as active ingredient are disclosed, which show high controlling activities for cucumber gray mold (*Botrytis cinerèa*), cucumber downey mildew (*Pseudoperonospora cubensis*), Alternaria sooty spot of Chinese mustard (*Alternaria brassicicola*), rice blast (*Pyricularia oryzae*), etc.

7 Claims, No Drawings

PYRIMIDINE DERIVATIVE, PROCESS FOR PREPARING SAME AND ARGICULTURAL OR HORTICULTURAL FUNGICIDAL COMPOSITION CONTAINING SAME

This is a continuation of application Ser. No. 924,384, filed Oct. 29, 1986, now U.S. Pat. No. 4,814,338.

FIELD OF THE INVENTION

This invention relates to pyrimidine derivatives and the salts thereof as well as an agricultural or horticultural fungicidal composition comprising the same as an active ingredient This invention also relates to a process for preparing the pyrimidine derivatives.

BACKGROUND OF THE INVENTION

Heretofore, with regard to 2-anilinopyrimidine derivatives there have been made many investigations, and chiefly in the field of fungicides there are known the active compounds. For instance, in East German Patent No. 151404 there is described the fungicidal action of 2-anilinopyrimidine derivatives represented by the general formula

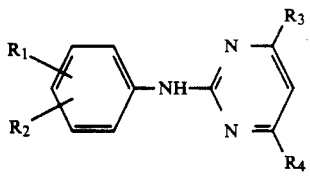

wherein $R^1$ and $R^2$ independently represent a hydrogen atom or an alkyl group which may be substituted, an aryl group, an aralkyl group, a halogen atom, a hydroxy group, an alkoxy group, an aryloxy group, a mercapto group, an alkylthio group, a carboxy group, an alkoxycarbonyl group, a carbamoyl group, a cyano group, a cyanato group, an isocyanato group, a thiocyanato group, an isothiocyanato group, a sulfo group, a halogenosulfonyl group, an amino group which may be substituted, a nitro group, or an acetyl group which may be substituted, and $R^3$ and $R^4$ represent a hydrogen atom or an alkyl group. Also, in British Patent No. 1245085 there is described the fungicidal action of pyrimidine derivatives represented by the general formula

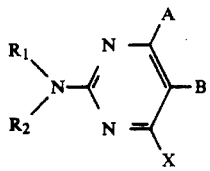

wherein A and B represent hydrogen, nitro, amino, halogen, hydrocarbon or substituted hydrocarbon groups, $R^1$ and $R^2$ represent hydrogen or organic groups, and X represents halogen.

These compounds are, however, found to have defects such that their fungicidal activity is weak, and moreover their anti-microbial spectrum is narrow

SUMMARY OF THE INVENTION

In an attempt to develop a useful agricultural or horticultural fungicide, various pyrimidine derivatives have been synthesized and investigated their physiological activities and as the result it has been discovered that the pyrimidine derivatives of this invention, represented by the general formula (I)

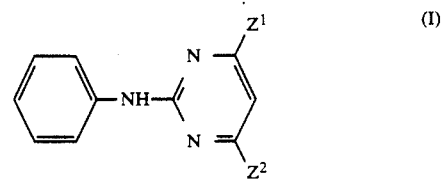

wherein $Z^1$ represents an alkynyl group, an alkenyl group, an alkoxy group, an alkenyloxy group, or an alkynyloxy group which may be substituted with a halogen atom, and $Z^2$ represents a hydrogen atom, a halogen atom, an alkyl group, an alkoxy group, or a group of formula

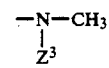

(wherein $Z^3$ represents a hydrogen atom or methyl group), have an excellent fungicidal activity for various plant pathogenic fungi, especially gray mold (*Botrytis cinerea*), and thus this invention has been accomplished.

DETAILED DESCRIPTION OF THE INVENTION

The pyrimidine derivatives of this invention and the salts thereof are represented by the general formula

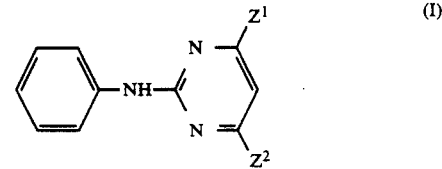

wherein $Z^1$ represents an alkynyl group having from 2 to 7 carbon atoms in which the position of the triple bond may be at any one of the 1- to 5-positions (e.g., an ethynyl group, a 1-propynyl group, a 2-propynyl group, a 1-butynyl group, a 3,3-dimethylbutynyl group, a 1-pentynyl group, a 2-pentynyl group, a 2-heptynyl group, etc ), an alkenyl group having from 2 to 5 carbon atoms in which the position of the double bond may be at any one of the 1- to 4-positions (e.g., a vinyl group, an alkyl group, a 1-propenyl group, a 2-butenyl group, a 2-pentenyl group, a 3-butenyl group, etc.), an alkoxy group having from 1 to 5 carbon atoms (e.g., a methoxy group, an ethoxy group, a propoxy group, an isopropoxy group, a butoxy group, a pentyloxy group, etc.), an alkenyloxy group having from 2 to 5 carbon atoms in which the position of the double bond may be at any one of the 1- to 4-positions (e.g , a vinyloxy group, an allyloxy group, a 2-butenyloxy group, a 2-pentenyloxy group, etc.), or an alkynyloxy group having from 3 to 5 carbon atoms in which the position of the triple bond may be at any one of the 2- to 4-positions which may be substituted with a halogen atom such a chlorine atom, a bromine atom, an iodine atom or a fluorine atom (e.g., a 2-propynyloxy group, a 2-butynyloxy group, a 2-pentynyloxy group, a 3-iodo-2-propynyloxy group, a 3-chloro-2-propynyloxy group, a 5-chloro-4pentynyloxy group, etc ), and $Z^2$ represents a hydrogen atom, a halogen atom (e.g., a chlorine atom, a bromine atom, ah iodine atom and a fluorine atom), an alkyl group having from 1 to 5 carbon atoms (e g., a methyl group, an ethyl group, a propyl group, an isopropyl group, a butyl group, an isobutyl group, a pentyl group etc.), an alkoxy group having from 1 to 5 carbon atoms (e.g., a methoxy group, an ethoxy group, a propoxy group, an isopropoxy group-,. etc ), or a group of formula

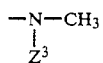

(wherein $Z^3$ represents a hydrogen atom o methyl group).

Preferably, $Z^1$ represents an alkoxy group, an alkynyl group or an alkynyloxy group which may be substituted with a halogen atom, $Z^2$ preferably represents a hydrogen atom, a halogen atom or an alkyl group Those compounds in which $Z^1$ represents a methoxy group, a propynyl group, a butynyl group, a propynyloxy group or a butynyloxy group, and $Z^2$ represents a hydrogen atom, a chlorine atom, a methyl group or an ethyl group are preferred. Those compounds in which $Z^1$ represents a 1-propynyl or 2-propynyloxy group and $Z^2$ represents a hydrogen atom, a chlorine atom, a methyl group or an ethyl group are more preferred, with those in which $Z^2$ represents a methyl group and an ethyl group being particularly preferred.

Specific examples of the compounds of this invention represented by the above described general formula (i) are listed in Table 1. The numbers of the compounds are referred to in the subsequent description.

TABLE 1

| Compound No. | $Z^1$ | $Z^2$ | Melting point or refractive index |
|---|---|---|---|
| 1 | —OCH₃ | —Cl | 101–103° C. |
| 2 | " | —OCH₃ | 71–75° C. |
| 3 | " | —H | 113–115° C. |
| 4 | " | —F | 82–84° C. |
| 5 | " | —CH₃ | 75–76° C. |
| 6 | " | —C₂H₅ | $n_D^{20}$ 1.6071 |
| 7 | " | —N(CH₃)₂ | 83–85° C. |
| 8 | " | —C₃H₇-(n) | $n_D^{20}$ 1.5970 |
| 9 | " | —NHCH₃ | 75–77° C. |
| 10 | " | —Br | 82–83.5° C. |
| 11 | " | —C₃H₇-(i) | $n_D^{20}$ 1.5953 |
| 12 | —OC₂H₅ | —Cl | 98–101° C. |
| 13 | " | —H | 105–106° C. |
| 14 | " | —CH₃ | 69–70° C. |
| 15 | " | —C₂H₅ | $n_D^{20}$ 1.5953 |
| 16 | —OC₃H₇-(n) | —Cl | 83–84° C. |
| 17 | —OC₃H₇-(i) | —Cl | 71–75° C. |
| 18 | —OCH₂CH=CH₂ | " | 80.5–83°0 C. |
| 19 | —OC₃H₇-(n) | —H | 69–71° C. |
| 20 | —OCH₃ | —Cl (sulfate) | 196–197° C. |
| 21 | —OC₃H₇-(n) | —CH₃ | $n_D^{20}$ 1.5973 |
| 22 | —OC₃H₇-(i) | —CH₃ | $n_D^{20}$ 1.5931 |
| 23 | —OCH₂CH=CH₂ | —CH₃ | $n_D^{20}$ 1.6098 |
| 24 | —C≡CH | —CH₃ | 86–88° C. |
| 25 | " | —C₂H₅ | 51–53° C. |
| 26 | —C≡CCH₃ | —H | 165–169° C. |
| 27(a) | " | —CH₃ | 125–127° C. |
| 27(b) | " | —CH₃ | 135–136° C. |
| 28 | " | —C₂H₅ | 90–91.5° C. |
| 29 | " | —Cl | 121–124° C. |
| 30 | " | —OCH₃ | 91–92° C. |
| 31 | —C≡CC₂H₅ | —H | 120–121° C. |
| 32 | " | —CH₃ | 120–122° C. |
| 33 | —C≡CCH₂CH₂CH₃ | " | 89–91° C. |
| 34 | —C≡CC(CH₃)₂CH₃ | —H | 130–131° C. |
| 35 | " | —CH₃ | 116–118° C. |
| 36 | —CH=CH₂ | " | 70.5–72° C. |
| 37 | —CH=CHCH₃ | " | $n_d^{20}$ 1.6408 |
| 38 | —OCH₂C≡CH | " | 72–74° C. |
| 39 | " | —Cl | 92–93° C. |
| 40 | —C≡CCH₃ | —N(CH₃)₂ | 150–152° C. |
| 41 | " | —CH₃ (sulfate) | 192–195 ° C. |

TABLE 1-continued

| Compound No. | $Z^1$ | $Z^2$ | Melting point or refractive index |
|---|---|---|---|
| 42 | " | —CH$_3$ (hydrochloride) | 140–144° C. (decomp. pt) |
| 43 | " | —CH$_3$ (nitrate) | 149–150° C. (decomp. pt) |
| 44 | —OCH$_2$C≡CI | —CH$_3$ | 160–161° C. |
| 45 | —C≡CH | —Cl | $n_D^{20}$ unmeasurable |
| 46 | —OCH$_2$C≡CCH$_3$ | —CH$_3$ | $n_D^{20}$ 1.6131 |
| 47 | —OCH$_3$ | —I | 93–95° C. |

Usually, the compounds of this invention can be prepared in the following manner.

Preparation Process 1

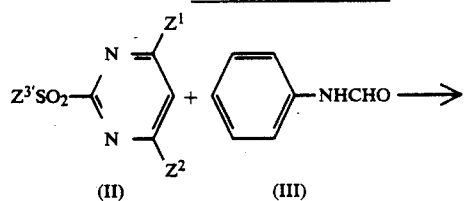

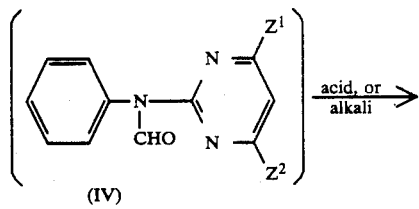

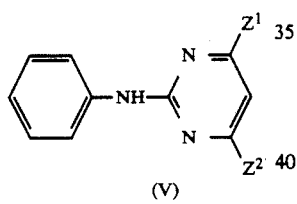

(V)

In the above formulae, $Z^{3'}$ represents an alkyl group, a benzyl group or a substituted benzyl group; $Z^1$ and $Z^2$ have the same meanings as defined above. The compound of formula (II) and formanilide (III) are reacted in a solvent (e.g., aromatic hydrocarbons such as benzene, toluene, xylene, etc., inert polar solvents such as dimethylformamide, dimethylacetamide, dimethyl sulfoxide, etc., halogenated hydrocarbons such as dichloromethane, chloroform, carbon tetrachloride, etc., ethers such as diethyl ether, dioxane, tetrahydrofuran, etc , ketones such as acetone, methyl ethyl ketone, cyclohexanone, etc., nitriles such as acetonitrile, propionitrile, etc.) in the presence of a base (e.g., alkali metals, alkali metal hydrides, alkali metal hydroxides, etc.) at a temperature of from −20° C. to the boiling point of the solvent used, preferably from room temperature to 100° C., to form an intermediate (IV). This intermediate (IV), with or without isolation, is hydrolyzed in water or a mixed solvent comprising water and an organic solvent in the presence of an acid such as hydrochloric acid, hydrobromic acid, sulfuric acid, etc., an alkali metal hydroxide such as sodium hydroxide, potassium hydroxide, etc., and the like at a temperature of from 0° C. to the boiling point of the solvent used to obtain the compound of this invention represented by formula (V). The compound of formula (V) can be reacted with an acid, e.g., hydrochloric acid, sulfuric acid and nitric acid to obtain salts thereof.

Of the compounds of this invention represented by formula (I), those in which $Z^1$ represents an alkoxy group, an alkenyloxy group or an alkynyloxy group which may be substituted with a halogen atom, and $Z^2$ represents an alkoxy group or a group of formula —NRCH$_3$ where R represents a hydrogen atom or a methyl group can be prepared by the following process Preparation Process 2

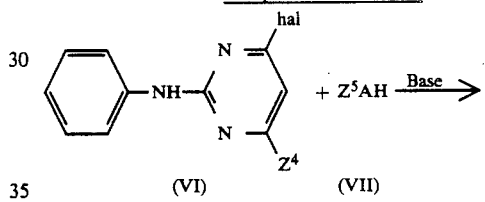

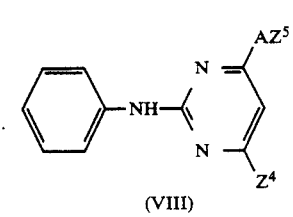

(VIII)

In the above formulae, hal represents a halogen atom, $Z^4$ represents a hydrogen atom, a halogen atom an alkyl group, an alkoxy group or an alkynyl group, $Z^5$ represents an alkyl group, an alkenyl group, an alkynyl group which may be substituted with a halogen atom, A represents an oxygen atom or a group of formula —NR— where R has the same meaning as defined above.

The compound of formula (VI) and the compound of formula (VII) are reacted preferably in a solvent (e.g., those described above for Preparation Process 1), or using an excessive amount of the alcohol as a solvent when A represents an oxygen atom, in the presence of a base (e.g., an alkali metal, an alkali metal hydroxide, carbonate and hydride, etc.) at a temperature of from −20° C. to the boiling point of the solvent used, preferably from room temperature to 100° C. to obtain the compound of this invention represented by formula (VIII).

More particularly, the compounds of this invention can be prepared as described hereinbelow.

When the compounds of this invention in which $Z^1$ is an alkoxy group, an alkenyloxy group, or an alkynyloxy group which may be substituted with a halogen atom can be prepared by the following process.

Preparation Process 3

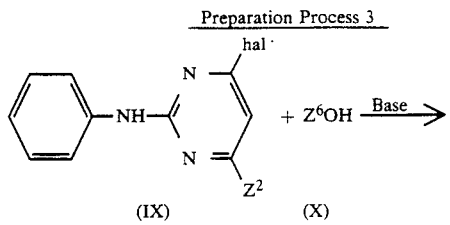

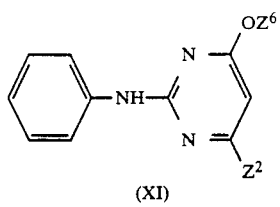

In the above formulae, hal represents a halogen atom, $Z^6$ represents an alkyl group or an alkenyl group, and $Z^2$ has the same meaning as defined above.

An 2-anilino-4 (or 6)-halogenopyrimidine (IX) and an alcohol (X) are reacted in the presence of a base (for instance, hydroxides, carbonates, hydrides, etc. of alkali metals, alkaline earth metals) preferably in a solvent (for instance, aromatic hydrocarbons such as benzene, toluene, xylene, etc.; inert polar solvents such as dimethylformamide, dimethylacetamide, dimethyl sulfoxide, etc.; halogenated hydrocarbons such as dichloromethane, chloroform, carbon tetrachloride, etc.; ethers such as diethyl ether, dioxane, tetrahydrofuran, etc.; ketones such as acetone, methyl ethyl ketone, cyclohexanone, etc.; nitriles such as acetonitrile, propionitrile, etc.), or alternatively the reaction is carried out using an alcohol (X) in excess as solvent without the use of other solvent. The compounds (XI) of this invention can be obtained by carrying out the reaction within the temperature range of from $-20°$ C. to the boiling point of the solvent, preferably from room temperature to 100° C.

Preparation Process 4

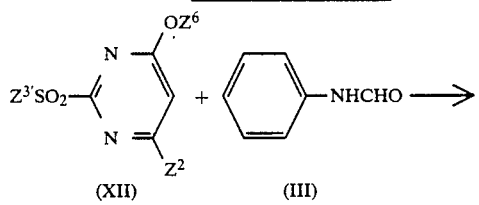

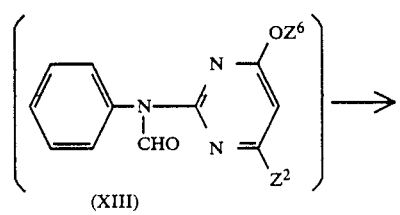

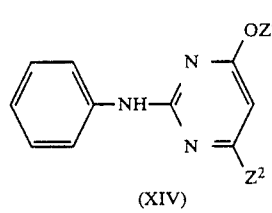

In the above formulae, $Z^2$, $Z^{3'}$ and $Z^6$ have the same meanings as defined above, and the parenthesized formula (XIII) represents an intermediate product in synthesis, which can also be isolated.

Compounds (XII) and formanilide (III) are reacted at a reaction temperature within the range of from $-20°$ C. to the boiling point of the solvent, preferably from room temperature to 100° C. in the presence of a base (e.g., alkali metals, alkali metal hydrides, alkali metal hydroxides, etc ) in a solvent (such as described in Preparation Process 1, except for alcohols) to give an intermediate product (XIII), which is subsequently hydrolyzed in a routine manner with an acid such as hydrochloric acid, hydrobromic acid, sulfuric acid, etc. or an alkali metal hydroxide such as sodium hydroxide, potassium hydroxide, etc to produce the compounds (X) of this invention.

The compounds obtained as above may be reacted with acids (such as hydrochloric acid, sulfuric acid, nitric acid) to form the salts.

Preparation Process 5

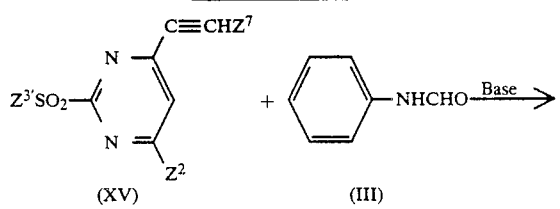

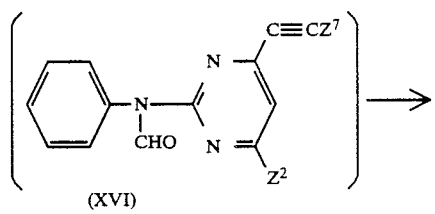

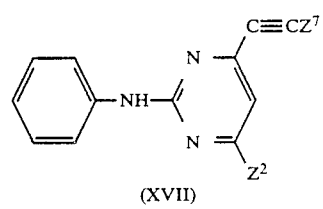

In the above formulae, $Z^7$ represents an alkyl group, $Z^2$ and $Z^3$ have the same meanings as defined above, and the parenthesized formula (XVI) represents an intermediate product in synthesis, which can also be isolated.

Compounds (XV) and formanilide (III) are reacted at a reaction temperature within the range of from $-20°$ C. to the boiling point of the solvent, preferably from room temperature to 100° C. in the presence of a base (e.g., alkali metals, alkali metal hydrides, alkali metal hydroxides, etc.) in a solvent (e.g., aromatic hydrocarbons such as benzene, toluene, xylene, etc.; inert polar solvents such as dimethylformamide, dimethylacetamide, dimethyl sulfoxide, etc.; halogenated hydrocarbons such as dichloromethane, chloroform, carbon tetrachloride, etc.; ethers such as diethyl ether, dioxane, tetrahydrofuran, etc.; ketones such as acetone, methyl ethyl ketone, cyclohexanone, etc.; nitriles such as acetonitrile, propionitrile, etc.) to give an intermediate product (XVI), which is subsequently hydrolyzed in a routine manner with an acid such as hydrochloric acid, hydrobromic acid, sulfuric acid, etc. or an alkali metal hydroxide such as sodium hydroxide, potassium hydroxide, etc. to produce the compounds (XVII) of this invention.

The compounds obtained as above may be reacted with acids (such as hydrochloric acid, sulfuric acid, nitric acid) to form the salts.

The compound of formula (XV) which is a starting material for preparing the compound of formula (XVII) can be obtained by oxidizing the compound of the following formula

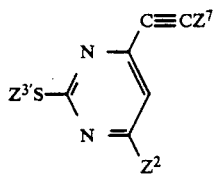

wherein $Z^2$, $Z^5$ and $Z^6$ have the same meanings above prepared by the method described in *Chemical and Pharmaceutical Bulletin*, 22, 3843 (1978) in a mixed solvent composed of an alcohol and water using an OXONE (registered trademark).

Preparation Process 6

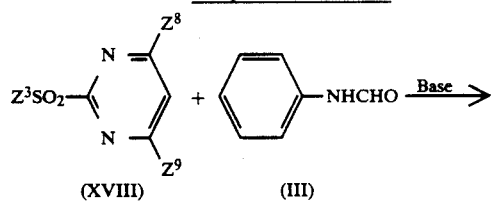

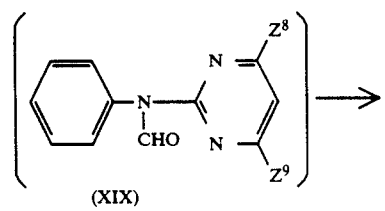

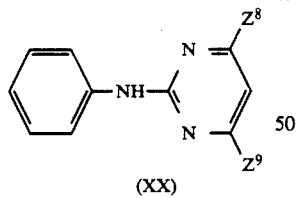

In the above formulae, $Z^8$ represents an alkynyl group, an alkenyl group or an alkynyloxy group which may be substituted with a halogen atom, $Z^9$ represents a hydrogen atom, a halogen atom, a lower alkyl group, a lower alkoxy group or a dimethylamino group, and $Z^{3'}$ represents an alkyl group, a benzyl group or a substituted benzyl group, and the parenthesized formula (XIX) represents an intermediate product in synthesis, which can also be isolated.

The compound of formula (XVIII) and formanilide (III) are reacted in the presence of a base (e.g., alkali metals alkali metal hydrides, alkali metal hydroxides, etc.) in a solvent (e.g., aromatic hydrocarbons such as benzene, toluene, xylene, etc., inert polar solvents such as dimethylformamide, dimethylacetamide, dimethyl sulfoxide, etc., halogenated hydrocarbons such as dichloromethane, chloroform, carbon tetrachloride, etc., ethers such as diethyl ether, dioxane, tetrahydrofuran, etc., ketones such as acetone, methyl ethyl ketone, cyclohexanone, etc., nitriles such as acetonitrile, propionitrile, etc.) at a temperature of from $-20°$ C. to the boiling point of the solvent used, preferably from room temperature to $100°$ C. to form an intermediate (XIX). This intermediate (XIX), with or without isolation, is hydrolyzed in water or a mixed solvent comprising water and an organic solvent in the presence of an acid such as hydrochloric acid, hydrobromic acid, sulfuric acid, etc., an alkali metal hydroxide such as sodium hydroxide, potassium hydroxide, etc., and the like at a temperature of from $0°$ C. to the boiling temperature of the solvent used to obtain the compound of this invention represented by formula (XX). The compound of formula (XX) can be reacted with an acid, e.g., hydrochloric acid, sulfuric acid and nitric acid to obtain salts thereof.

Preparation Process 7

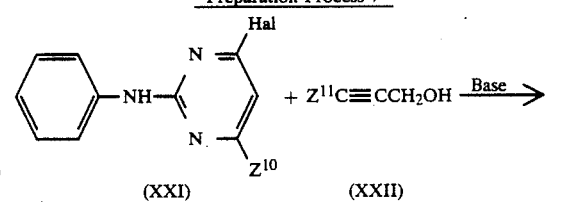

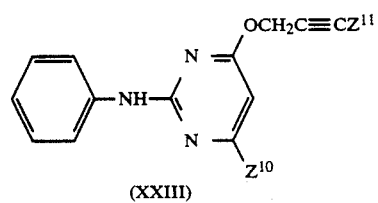

In the above formulae, $Z^{10}$ represents a halogen atom or a lower alkyl group, $Z^{11}$ represents a hydrogen atom or a halogen atom, $Z^{12}$ represents an alkynyloxy group which may be substituted with a halogen atom, $Z^{13}$ represents a lower alkoxy group or a dimethylamino group, and Hal represents a halogen atom. The above described reaction can be carried out in the presence of a base (e.g., alkali metal hydroxides, carbonates, hydrides, etc.) when the compound of formula (XXII) or (XXV) is an alcohol, or in the presence of sodium carbonate, sodium hydrogencarbonate, potassium hydrogencarbonate, or a tertiary amine such as triethylamine, or by the use of the amine derivative itself used in the reaction when the compound of formula (XXV) is dimethylamine. As the solvents, there can be used aromatic hydrocarbons such as benzene, toluene, xylene, etc.; inert polar solvents such as dimethylformamide, dimethylacetamide, dimethyl sulfoxide, etc.; halogenated hydrocarbons such as dichloromethane, chloroform, carbon tetrachloride, etc.; ethers such as diethyl ether, dioxane, tetrahydrofuran, etc.; ketones such as acetone, methyl ethyl ketone, cyclohexanone, etc.; nitriles such as acetonitrile, propionitrile, etc.; or water When alcohols are used as a reactant, excess amount of the alcohol can be used as a solvent.

The reaction temperature is within the range of from −20° C. to the boiling point of the solvent, preferably from room temperature to 100° C.

Now, with reference to concrete examples this invention will be explained in greater detail below

EXAMPLE 1

Preparation of 2-anilino-4-methyl-6-methoxypyrimidine (Compound 5)

2.9 g of 28% methanolic solution of sodium methylate was dissolved in 40 ml of methanol, and thereto was added 3.3 g of 2-anilino-4-chloro-6-methylpyrimidine. After 2 hours of reaction with stirring at room temperature the reaction liquid was poured in water The solids deposited were filtered, dried, and recrystallized from n-hexane to afford 2 9 g of 2-anilino-4-methyl-6-methoxypyrimidine (yield 92 %). Melting point: 75°–76° C.

EXAMPLE 2

Preparation of 2-anilino-4-chloro-6-methoxypyrimidine (Compound 1)

1.8 g of formanilide was dissolved in 50 ml of tetrahydrofuran, and 0.4 g of sodium hydride from which the oily matter had been removed beforehand with n-hexane was slowly added to the resulting solution at 10° to 20° C. while cooling with ice water. To the suspension thus obtained was added 3 3 g of 4-chloro-2-methanesulfonyl-6-methoxypyrimidine, and the mixture was stirred for 1 hour at room temperature. Then, 15 ml of 4N hydrochloric acid was added, and reaction was effected for 1 hour under reflux. The reaction liquid was poured in water, extracted with ether, and the ether layer was washed with water, dried over magnesium sulfate, and then the ether was stripped by concentration The residual crystals were recrystallized from n-hexane, and 4.0 g of 2-anilino-4-chloro-6-methoxypyrimidine was obtained (yield 87%). Melting point: 101°–103° C.

EXAMPLE 3

Preparation of 2-anilino-4-methyl-6-propynyl)pyrimidine (Compound 27)

2 1 g of formanilide was dissolved in 50 ml of dry benzene, and 0.4 g of sodium hydride from which the oily matter had been removed beforehand with n-hexane was slowly added to the resulting solution at 10° to 20° C., cooling with ice water. After 1 hour of stirring at room temperature, 3.2 g of 2-methanesulfonyl-4-methyl-6-(1-propynyl)pyrimidine was added to the suspension thus obtained, and the mixture was stirred for 10 hours at room temperature. To the reaction liquid was added 100 ml of benzene, and the benzene layer was washed with water, dried over Glauber's salt, and concentrated. Then the residue was dissolved in 100 ml of ethanol, and stirred for 10 hours at room temperature with the addition of 5 ml of 6N hydrochloric acid. The reaction liquid was poured in water, extracted with benzene, and the benzene layer was washed with water, dried with Glauber's salt, and concentrated. The residue was cooled to room temperature to solidify, thus giving rise to crystals having a melting point 135° –136° C. (Compound a).

Further, the crystals thus obtained were dissolved in benzene and the benzene layer was washed with an aqueous solution of sodium bicarbonate and with water, dried over Glauber's salt and concentrated, and recrystallized from ethanol-hexane to obtain crystals having a melting point of 125° to 127° C. (Compound b). Both the compounds a and b were confirmed to be 2-anilino-4-methyl-6-(1-propynyl)pyrimidine by Infrared spectral analysis, NMR and elemental analysis.

|  | Compound a |
|---|---|
| IR (cm$^{-1}$): | NH 3270; C≡C 2230 |
| NMR (CDCl$_3$): | :2.05 (3H, s), 2.39 (3H, s), 6.59 (1H, s), 6.80–7.70 (6H, m) |
| Elemental Analysis: | |
| Calculated (%): | C:75.31, H:5.87, N:18.82 |
| Found (%): | C:75.89, H:6.05, N:18.53 |
|  | Compound b |
| IR (cm$^{-1}$): | NH 3270, C≡C 2230 |
| NMR(CDCl$_3$): | :2.05 (3H, s), 2.39 (3H, s), 6.60 (1H, s), 6.82–7.70 (6H, m) |
| Elemental Analysis: | |
| Calculated (%): | C:75.31, H:5.87, N:18.82 |
| Found (%): | C:74.95, H:5.88, N:18.55 |

EXAMPLE 4

Preparation of 2-anilino-4-methyl-6-(1-propenyl)pyrimidine (Compound 37)

0.42 g of NaH from which the oily matter had been removed beforehand with n-hexane was suspended in 70 ml of THF, and then stirred for 1 hour under reflux with the addition of 2.0 g of formanilide. After cooling 3.6 g of 2-methanesulfonyl-4-methyl-6-(1-propenyl)-pyrimidine was added and stirred for 1 hour at room temperature. Then, 20 ml of 10% aqueous solution of sodium hydroxide was added, and the mixture was stirred for 2 hours at room temperature. The reaction liquid was poured in water and neutralized with dilute hydrochloric acid. The organic layer was extracted with ethyl acetate, and dried over magnesium sulfate. The ethyl acetate was stripped under reduced pressure. The residue was purified by silica gel column chromatography, and 2.7 g of 2-anilino-4-methyl-6-(1-propenyl)pyrimidine was obtained (yield 72%). Refractive index: 1.6408 (20° C.).

EXAMPLE 5

Preparation of 2-anilino-4-chloro-6-(1-propynyl)pyrimidine (Compound 29)

After 3.0 g of formanilide was dissolved in 70 ml of dry benzene, 0.55 g of NaH from which the oily matter had been removed beforehand with n-hexane was slowly added at 10° to 20° C., and the mixture was stirred for 1 hour at room temperature 2-Methanesulfonyl-4-chloro-6-(1-propynyl)pyrimidine (4.4 g) was added to the suspension thus obtained and the mixture was stirred for 10 hours at room temperature. The reaction liquid was washed with water, dried, concentrated, and then stirred for 10 hours at room temperature with the addition of 100 ml of ethanol and 5 ml of 6N hydrochloric acid. To the reaction mixture was added 150 ml of toluene and the toluene layer was washed with water, dried, concentrated, and the residue was purified by silica gel column chromatography, whereby 3 6 g of 2-anilino-4-chloro-6-(1-propynyl)pyrimidine was obtained (yield 75%) Melting point: 121°–124° C.

EXAMPLE 6

Preparation of
2-anilino-4-chloro-6-(2-propynyloxy)pyrimidine
(Compound 39)

NaH (1.0 g) from which the oily matter had been removed beforehand with n-hexane was suspended in 30 ml of DMF and 2.4 g of 2-propynyl alcohol was added to the suspension, and the mixture was stirred for 30 minutes at room temperature. Then the solution was dropwise added to a solution obtained by dissolving 5.0 g of 2-anilino-4 6-dichloropyrimidine in 50 ml of DMF. After 7 hours of stirring at room temperature the reaction liquid was poured in water, and rendered weakly acidic with dilute hydrochloric acid. The organic layer was extracted with toluene, and dried over magnesium sulfate. Toluene was stripped under reduced pressure, and the residue was purified by silica gel column chromatography, whereby 3.5 g of 2-anilino-4-chloro-6-(2-propynyloxy)pyrimidine was obtained (yield 65%). Melting point 92°–93° C.

EXAMPLE 7

Preparation of
2-anilino-4-methyl-6-(1-propynyl)pyrimidine sulfate
(Compound 41)

2-Anilino-4-methyl-6-(1-propynyl)pyrimidine (2.2 g) was dissolved in 100 ml of ethanol, and 2 ml of concentrated sulfuric acid was added thereto and stirred for 1 hour at room temperature. The crystals deposited were filtered, and dried to afford 2.4 g of 2-anilino-4-methyl-6-(1-propynyl)pyrimidine sulfate (yield 75%). Melting point: 192°–195° C.

EXAMPLE 8

Preparation of
2-anilino-4-dimethylamino-6-(1-propynyl)pyrimidine
(Compound 40)

2-Anilino-4-chloro-6-(1-propynyl)pyrimidine (1.7 g) prepared in Example 2, 1.9 g of 54% aqueous solution of dimethylamine and 0.7 g of KOH were added to 20 ml of THF and the mixture was stirred at room temperature for 24 hours. The reaction liquid was poured in water and extracted with benzene. Then, the benzen layer was dried over Glauber's salt and concentrated, the residue was recrystallized from n-hexane-ethanol to afford 1.5 g of 2-anilino-4-dimethylamino-6-(1-propynyl)pyrimidine (yield: 85%). Melting point: 150°–152° C.

EXAMPLE 9

Preparation of
2-anilino-4-methyl-6-isopropoxypyrimidine
(Compound 22)

In the same manner as in Example 3, 3.1 g of 2-anilino-4-chloro-6-methylpyrimidine, 1.9 g of isopropyl alcohol and 0.7 g of NaH were added to 50 ml of THF and allowed to react at room temperature for 4 hours to obtain 2.2 g of 2-anilino-4-methyl-6-isopropoxypyrimidine (yield 65%). $n^{20}_D$ 1.5931.

The agricultural or horticultural fungicide of this invention is a composition comprising a pyrimidine derivative or the salt thereof as the active ingredient. The compounds of this invention can be used as such, but are usually compounded with a carrier, a surface active agent, a dispersant, an adjuvant, etc and then formulated into the form of dust, wettable powder, emulsifiable concentrate, fine grains, or granules. Examples of suitable carrier include, for instance, solid carriers such as talc, bentonite, clay, kaoline, diatomaceous earth, white carbon, vermiculite, slaked lime, silica sand, ammonium sulfate, urea, etc. and liquid carriers such as methylnaphthalene, isopropyl alcohol, xylene, cyclohexanone, etc. Examples of surface active agent and dispersant include, for instance, dinaphthylmethanedisulfonate, alkyl sulfates, alkylarylsulfonates, alkylsulfonates, lignin sulfonate, polyoxyethylene glycol ethers, polyoxyethylene alkyl aryl ethers, polyoxyethylene sorbitan monoalkylates, etc.

These preparations are diluted to a suitable concentration and sprayed, dusted, or directly applied.

Usually, the fungicide of this invention can be applied in an amount of from about 1 g to about 100 kg per hectare, preferably 10 g to 10 kg per hectare. When it is sprayed to leaves and stems of plants it is usually diluted to a concentration of about 0.1 to 10,000 ppm, preferably 100 to 3,000 ppm.

EXAMPLE 10

(Dust)

2% of compound 1, 5% of diatomaceous earth, and 93% of clay were homogeneously mixed and pulverized to prepare a dust.

EXAMPLE 11

(Wettable Powder)

50% of Compound 4, 45% of diatomaceous earth, 2% of sodium dinaphthylmethanedisulfonate, and 3% of sodium lignin sulfonate were homogeneously mixed and pulverized to prepare a wettable powder.

EXAMPLE 12

(Emulsifiable Concentrate)

30% of Compound 5, 20% of cyclohexanone, 11% of polyoxyethylene alkyl aryl ether, 4% of calcium alkylbenzenesulfonate, and 35% of methylnaphthalene were homogeneously dissolved to prepare an emulsifiable concentrate.

EXAMPLE 13

(Granules)

5% of Compound 22, 2% of sodium lauryl sulfate, 5% of sodium lignin sulfonate, 2% of carboxymethylcellulose, and 86% of clay were homogeneously mixed and pulverized. To the resulting mixture was added 20% of water, and the mixture was kneaded, processed into granular form of 14 to 32 mesh using an extruder type granulating machine and dried to prepare granules.

EXAMPLE 14

(Dust)

2% of Compound 23, 5% of diatomaceous earth, and 93% of clay were homogeneously mixed and pulverized to prepare a dust.

EXAMPLE 15

(Wettable Powder)

50% of Compound 24, 45% of diatomaceous earth, 2% of sodium dinaphthylmethane disulfonate, and 3% of sodium lignin sulfonate were homogeneously mixed and pulverized to prepare a wettable powder.

EXAMPLE 16

(Emulsifiable Concentrate)

30% of Compound 25, 20% of cyclohexanone, 11% of polyoxyethylene alkyl aryl ether, 4% of calcium alkylbenzenesulfonate, and 35% of methylnaphthalene were homogeneously dissolved to prepare an emulsifiable concentration.

EXAMPLE 17

(Granules)

5% of Compound 26, 2% of sodium lauryl sulfate, 5% of sodium lignin sulfonate, 2% of carboxymethylcellulose, and 86% of clay were homogeneously mixed and pulverized. To 100 parts by weight of the resulting mixture was added 20 parts by weight of water and the mixture was kneaded, processed into granular form of 14 to 32 mesh using an extruder type granulating machine, and dried to prepare granules.

The agricultural or horticultural fungicidal composition of this invention possesses a broad antimicrobial spectrum showing an excellent activity as the controlling agents especially for rice blast (*Pyricularia oryzae*), cucumber downy mildew (*Pseudoperonospora cubensis*), cucumber gray mold (*Botrytis cinerea*), and Alternaria sooty spot of Chinese mustard (*Alternaria brassicicola*), and is also effective as the controlling agents for rice sheath blight (*Rhizoctonia solani*), cucumber anthracnose (*Colletotrichum lagenarium*), and apple Alternaria leaf spot (*Alternaria mali*).

The agricultural or horticultural fungicidal compositions of this invention show high controlling activities for cucumber gray mold, cucumber downy mildew, Alternaria sooty spot of Chinese mustard, rice blast, etc. even as compared with the compounds described in the above described East German Patent No. 151404 and British Patent No. 1245085. Moreover, the agricultural or horticultural fungicidal compositions of this invention are also characterized by that they are no harmful chemicals and yet excellent in the residual activity and persistence to rainfall, and not only the toxicity to warm-blooded animals but also the fish-toxicity is weak.

Among the agricultural or horticultural fungicidal composition of this invention, preferred are those which contain 2-anilino-4-methoxy-6-methylpyrimidine, 2-anilino-4-(1-propynyl)pyrimidine, 2-anilino-4-methyl-6-(1-propynyl)pyrimidine, 2-anilino-4-propynyl)pyrimidine, 2-anilino-4-chloro-6-(1-propynyl)pyrimidine, 2-anilino-4-(1-butynyl)-6-methylpyrimidine, 2-anilino-4-methyl-6-(2-propynyloxy)pyrimidine, 2-anilino-4-chloro-6-methoxy-pyrimidine, etc.

With reference to some Test Examples the effect achieved by the agricultural or horticultural fungicidal composition of this invention will be explained more concretely below.

TEST EXAMPLE 1

Test on the Effect of Controlling Cucumber Gray Mold

When the cucumber (variety: "Sagami hanjiro") which was grown by seeding in a population of 12 seeds per pot (square pot of 9 cm side) attained to the cotyledonous stage, a wettable powder prepared as in Example 11 was diluted to a predetermined concentration with water, and sprayed with a spray gun in an amount of 5 ml per pot. After the air drying of the sprayed liquid, a homogenized solution of the liquid cultured fungi of cucumber gray mold (*Botrytis cinerea*) was inoculated by spraying. After three days of incubation in a moistured chamber, the number of the infected leaves was examined according to the following standard. The results are shown in Tables 2, 3, 4 and 5.

| Standard of Test | |
|---|---|
| Infection Index 0: | No leaf spot |
| Infection Index 1: | Infected area is less than ⅛ of leaf |
| Infection Index 2: | Infected area is in the range of ⅛ to ⅝ of leaf surface area |
| Infection Index 3: | Infected area is more than ⅝ of leaf surface area |

$$\text{Incidence of Disease (\%)} = \frac{\text{(Infection Index} \times \text{Number of Leaves)}}{3 \times \text{Number of Examined Leaves}} \times 100$$

$$\text{Controlling Activity (\%)} = \left(1 - \frac{\text{Incidence of Disease in Treated}}{\text{Incidence of Disease in Untreated}}\right) \times 100$$

In addition, the following fungicidal compounds were used for comparison.

Comparative Compound A:

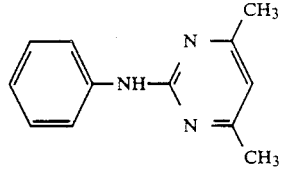

(Compound described in East German Patent 151404)

Comparative Compound B:

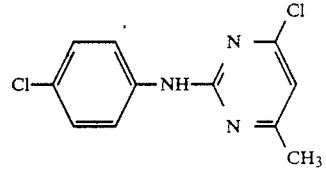

(Compound described in British Patent 1245085)

TABLE 2

| Compound Tested | Concentration (ppm) | Controlling Activity (%) |
|---|---|---|
| Compound 1 | 50 | 100 |
| Compound 3 | 50 | 100 |
| Compound 4 | 50 | 100 |

TABLE 2-continued

| Compound Tested | Concentration (ppm) | Controlling Activity (%) |
|---|---|---|
| Compound 5 | 50 | 100 |
| Compound 6 | 50 | 100 |
| Compound 9 | 50 | 82 |
| Compound 10 | 50 | 89 |
| Compound 13 | 50 | 100 |
| Compound 14 | 50 | 100 |
| Compound 15 | 50 | 90 |
| Compound 20 | 50 | 100 |
| Comparative Compound A | 50 | 80 |
| Comparative Compound B | 50 | 20 |
| Untreated | — | 0 |

TABLE 3

| Compound Tested | Concentration (ppm) | Controlling Activity (%) |
|---|---|---|
| Compound 24 | 50 | 100 |
| Compound 25 | 50 | 88 |
| Compound 26 | 50 | 100 |
| Compound 27(a) | 50 | 100 |
| Compound 28 | 50 | 100 |
| Compound 29 | 50 | 99.3 |
| Compound 32 | 50 | 100 |
| Compound 36 | 50 | 88.2 |
| Compound 37 | 50 | 100 |
| Compound 38 | 50 | 100 |
| Compound 41 | 50 | 100 |
| Compound 44 | 50 | 87.3 |
| Comparative Compound A | 50 | 77.3 |
| Comparative Compound B | 50 | 19.5 |
| Untreated | — | 0 |

TABLE 4

| Compound Tested | Concentration (ppm) | Controlling Activity (%) |
|---|---|---|
| Compound 21 | 50 | 100 |
| Compound 23 | 50 | 100 |
| Compound 27(a) | 50 | 100 |
| Compound 27(b) | 50 | 100 |
| Compound 46 | 50 | 100 |
| Comparative Compound A | 50 | 91.7 |
| Comparative Compound B | 50 | 35.9 |
| Untreated | — | 0 |

TABLE 5

| Compound Tested | Concentration (ppm) | Controlling Activity (%) |
|---|---|---|
| Compound 26 | 10 | 86.0 |
|  | 30 | 100 |
| Compound 27(a) | 10 | 100 |
|  | 30 | 100 |
| Compound 28 | 10 | 54.5 |
|  | 30 | 99.4 |
| Compound 29 | 10 | 60.4 |
|  | 30 | 97.5 |
| Compound 32 | 10 | 60.3 |
|  | 30 | 99.9 |
| Compound 38 | 10 | 72.4 |
|  | 30 | 99.5 |
| IPRODIONE | 10 | 16.7 |
|  | 30 | 70.7 |
| Untreated | — | 0 |

TEST EXAMPLE 2

Test on the Effect of Controlling Alternaria Sooty Spot of Chinese Mustard

When the Chinese mustard (variety: Okute Komatsuna) which was grown by seeding in a population of 15 seeds per pot (square pot of 9 cm side) attained to the cotyledonous stage, a wettable powder prepared as in Example 11 was diluted to 500 ppm with water, and sprayed in an amount of 5 ml per pot. After the air drying of the sprayed liquid, the fungi of Alternaria sooty spot (*Alternaria brassicicola*), which were cultured for one week in a PSA medium and the spore concentration was adjusted to 60 to 80 spores per visual field of a microscope (150 magnifications), were inoculated by spraying. After the inoculation the plant was incubated for 3 days in a moistured chamber (30° C.), and the number of the leaf spots was counted, and the control value was calculated from the average number of the spots per leaf according to the following equation.

Controlling Activity (%) =

$$\left(1 - \frac{\text{Average Number of Spots in Treated}}{\text{Average Number of Spots in Untreated}}\right) \times 100$$

The results are shown in Tables 6 to 8.

TABLE 6

| Compound Tested | Controlling Activity (%) |
|---|---|
| Compound 1 | 65 |
| Compound 3 | 72 |
| Compound 4 | 80 |
| Compound 5 | 95 |
| Compound 6 | 80 |
| Compound 7 | 97 |
| Compound 10 | 83 |
| Compound 12 | 96 |
| Compound 13 | 68 |
| Compound 14 | 98 |
| Compound 16 | 90 |
| Compound 17 | 98 |
| Compound 18 | 93 |
| Compound 20 | 78 |
| Comparative Compound A | 0 |
| Untreated | 0 |

TABLE 7

| Compound Tested | Controlling Activity (%) |
|---|---|
| Compound 25 | 72.5 |
| Compound 28 | 79.6 |
| Compound 30 | 72.6 |
| Compound 36 | 69.1 |
| Compound 38 | 95.8 |
| Compound 39 | 73.5 |
| Compound 40 | 81.7 |
| Compound 44 | 92.5 |
| Comparative Compound A | 0 |
| Untreated | 0 |

TABLE 8

| Compound Tested | Controlling Activity (%) |
|---|---|
| Compound 21 | 84.8 |

TABLE 8-continued

| Compound Tested | Controlling Activity (%) |
|---|---|
| Compound 22 | 93.8 |
| Compound 23 | 98.9 |
| Compound 45 | 72.8 |
| Compound 46 | 92.7 |
| Compound 47 | 93.0 |
| Comparative Compound A | 0 |
| Untreated | 0 |

TEST EXAMPLE 3

Test on the Effect of Controlling Cucumber Downy Mildew

When the cucumber (variety: "Sagami hanjiro") which was grown by seeding in a population of 12 seeds per pot (square pot of 9 cm side) attained to the cotyledonous stage, a wettable powder prepared as in Example 11 was diluted to 500 ppm with water, and sprayed with a spray gun in an amount of 5 ml per pot. After the air drying of the sprayed liquid, the fungi of cucumber downy mildew (Pseudoperonospcra cubensis) whose spore concentration had been adjusted to 5 to 10 spores per visual field of a microscope (150 magnifications), were inoculated by spraying. Twenty four (24) hours after the inoculation, the plant was allowed to be infected by being placed on a bench in a greenhouse, and seven days after the inoculation it was examined according to the following standard.

Healthy : No infection is discernible.
Slight : Infected area is less than $\frac{1}{3}$
Moderate : Infected area is $\frac{1}{3}$ to $\frac{2}{3}$
Severe : Infected area is more than $\frac{2}{3}$ Incidence of Disease (%) =

$$\frac{(Healthy \times 0) + (Slight \times 1) + (Moderate \times 2) + (Severe \times 3)}{Number\ of\ All\ Examined\ Leaves \times 3} \times 100$$

Controlling Activity (%) =

$$\left(1 - \frac{Incidence\ of\ Disease\ in\ Treated}{Incidence\ of\ Disease\ in\ Untreated}\right) \times 100$$

The results are shown in Tables 9 and 10.

TABLE 9

| Compound Tested | Controlling Activity (%) |
|---|---|
| Compound 3 | 95 |
| Compound 4 | 95 |
| Compound 6 | 75 |
| Compound 10 | 77 |
| Compound 14 | 77 |
| Compound 15 | 100 |
| Compound 17 | 97 |
| Compound 18 | 75 |
| Comparative Compound A | 0 |
| Comparative Compound B | 0 |
| Untreated | 0 |

TABLE 10

| Compound Tested | Controlling Activity (%) |
|---|---|
| Compound 21 | 75 |
| Compound 23 | 66.7 |
| Compound 38 | 75 |
| Compound 43 | 90 |
| Compound 46 | 66.7 |
| Comparative Compound A | 0 |
| Comparative Compound B | 0 |
| Untreated | 0 |

TEST EXAMPLE 4

Test on the Effect of Controlling Rice Blast

Twenty grains of rice seed (variety Aichi asahi) were sowed in each white porcelain pot (diameter: 9 cm) and grown for 3 to 4 weeks in a greenhouse. When the seedling developed 4th leaf, a wettable powder prepared as in Example 11 was diluted to 500 ppm with water, and sprayed with a spray gun in an amount of 10 ml per pot. After the air drying of the sprayed liquid, a suspension of spores of rice blast (Pyricularica oryzae) was inoculated by spraying and the pot was placed in a moistured chamber at 25° C. After five days from the inoculation the number of lesions was examined.

Controlling Activity (%) =

$$\left(1 - \frac{Number\ of\ Lesions\ in\ Treated}{Number\ of\ Lesions\ in\ Untreated}\right) \times 100$$

The results obtained are shown in Tables 11 and 12.

TABLE 11

| Compound Tested | Controlling Activity (%) |
|---|---|
| Compound 2 | 100 |
| Compound 8 | 75.1 |
| Compound 17 | 84.3 |
| Compound 18 | 50 |
| Comparative Compound A | 0 |
| Untreated | 0 |

TABLE 12

| Compound Tested | Controlling Activity (%) |
|---|---|
| Compound 21 | 77.7 |
| Compound 22 | 83.9 |
| Compound 23 | 80.2 |
| Compound 28 | 75.2 |
| Compound 29 | 85.5 |
| Compound 30 | 78.6 |
| Compound 36 | 87.0 |
| Compound 38 | 67.8 |
| Compound 40 | 91.5 |
| Compound 41 | 100 |
| Compound 43 | 86.3 |
| Compound 44 | 74 |
| Compound 45 | 100 |
| Compound 46 | 80 |
| Comparative Compound A | 0 |
| Untreated | 0 |

TEST EXAMPLE 5

Test on the Effect of Controlling Rice Sheath Blight

Fifteen (15) grains of paddy field rice plant (variety: (Kinmaze)) were sowed in an unglazed pot (diameter: 7 cm) and grown in a greenhouse for 4 to 5 weeks. When the seedling developed 5th leaf, a wettable powder prepared as in Example 11 was diluted to 500 ppm with water and sprayed in an amount of 10 ml per pot. After the air drying of the sprayed liquid the fungus of rice sheath blight (*Rhizoctonia solani*) cultured on a chaffs-bran medium for seven days was inoculated at the foot of the plant and the pot was placed in a moistured chamber at 28° C. After five days from the inoculation, the height of the lesions formed at the leaf sheath of the plant was measured, and control value was calculated according to the following equation.

Controlling Activity (%) =

$$\left(1 - \frac{\text{Height of Lesions of Treated}}{\text{Height of Lesions of Untreated}}\right) \times 100$$

The results obtained are shown in Table 13.

TABLE 13

| Compound Tested | Controlling Activity (%) |
| --- | --- |
| Compound 21 | 95.9 |
| Compound 23 | 74.0 |
| Compound 25 | 75.2 |
| Compound 26 | 80.9 |
| Compound 28 | 62 |
| Compound 32 | 92.3 |
| Compound 33 | 96.5 |
| Compound 34 | 91.2 |
| Compound 35 | 96.5 |
| Compound 36 | 69.9 |
| Compound 37 | 93.2 |
| Compound 38 | 88 |
| Compound 42 | 76.6 |
| Compound 44 | 90.4 |
| Compound 45 | 71.4 |
| Compound 46 | 100 |
| Comparative Compound A | 25.2 |
| Untreated | 0 |

While the invention has been described in detail and with reference to specific embodiment thereof, it will be apparent to one skilled in the art that various changes and modifications can be made therein without departing from the spirit and scope thereof.

What is claimed is:

1. A pyrimidine derivative represented by formula (I)

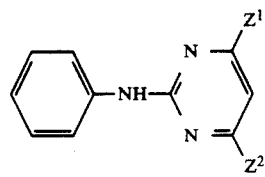

wherein $Z^1$ represents an alkenyl group, an alkoxy group, an alkenyloxy group, or an alkylnyloxy group which may be substituted with halogen atom, and $Z^2$ represents a hydrogen atom, a halogen atom, an alkyl group, an alkoxy group, or a group of the formula

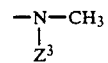

where $Z^3$ represents a hydrogen atom or an agricultural or horticultural, fungicidally acceptable salt thereof.

2. The pyrimidine derivative as claimed in claim 1, wherein $Z^1$ represents an alkoxy group or an alkynyloxy group which may be substituted with a halogen atom.

3. The pyrimidine derivative as claimed in claim 1, wherein $Z^2$ represents a hydrogen atom, a halogen atom or a lower alkyl group.

4. The pyrimidine derivative as claimed in claim 1, wherein $Z^1$ represents a methoxy group a propynyloxy group or a butynyloxy group, and $Z^2$ represents a hydrogen atom, a chlorine atom, a methyl group or an ethyl group.

5. The pyrimidine derivative as claimed in claim 1, wherein $Z^1$ represents a 2-propynyloxy group and $Z^2$ represents a hydrogen atom, a chlorine atom, a methyl group or an ethyl group.

6. An agricultural or horticultural fungicidal composition comprising as an active ingredient a pyrimidine derivative represented by the formula (I)

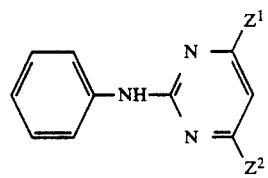

wherein $Z^1$ represents an alkenyl group, an alkoxy group, an alkenyloxy group, or an alkynyloxy group which may be substituted with a halogen atom, and $Z^2$ represents a hydrogen atom, a halogen atom, an alkyl group, an alkoxy group, or a group of the formula

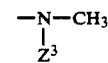

where $Z^3$ represents a hydrogen atom or a methyl group; or an agricultural or horticultural, fungicidally acceptable salt thereof, and a carrier.

7. A method of protecting plants against agricultural or horticultural fungi, which comprises applying a fungicidally effective amount of a pyrimidine derivative represented by formula (I)

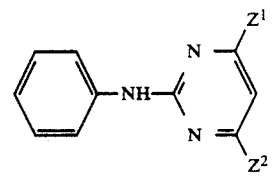

wherein $Z^1$ represents an alkenyl group, an alkoxy group, an alkenyloxy group, or an alkynyloxy group which may be substituted with a halogen atom, and $Z^2$ represents a hydrogen atom, a halogen atom, an alkyl group, an alkoxy group, or a group of the formula

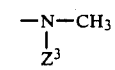

where $Z^3$ represents a hydrogen atom or a methyl group; or an agricultural or horticultural fungicidally acceptable salt thereof.

* * * * *